United States Patent
Stout et al.

(10) Patent No.: US 8,721,672 B2
(45) Date of Patent: May 13, 2014

(54) VARIABLE FIT LANCET

(75) Inventors: Jeffrey T. Stout, Smyrna, GA (US); Michael V. Lipoma, Villa Rica, GA (US); Christopher J. Ruf, Marietta, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 731 days.

(21) Appl. No.: 12/667,155

(22) PCT Filed: Jul. 1, 2008

(86) PCT No.: PCT/US2008/068884
§ 371 (c)(1),
(2), (4) Date: Dec. 29, 2009

(87) PCT Pub. No.: WO2009/006461
PCT Pub. Date: Jan. 8, 2009

(65) Prior Publication Data
US 2011/0009891 A1 Jan. 13, 2011

Related U.S. Application Data

(60) Provisional application No. 60/947,688, filed on Jul. 3, 2007.

(51) Int. Cl.
*A61B 17/32* (2006.01)
*A61B 5/15* (2006.01)
(52) U.S. Cl.
CPC .................................... *A61B 5/1411* (2013.01)
USPC ....................................................... 606/181

(58) Field of Classification Search
CPC ............... A61B 5/1411; A61B 5/1405; A61B 5/150435; A61B 5/150259; A61B 5/150412
USPC ............ 606/181–183, 185; 604/272; 600/583
See application file for complete search history.

(56) References Cited

U.S. PATENT DOCUMENTS

| | | | |
|---|---|---|---|
| 3,358,689 A | 12/1967 | Higgins | |
| 4,624,253 A | 11/1986 | Burns | |
| 5,314,442 A * | 5/1994 | Morita | ........................ 606/182 |

(Continued)

FOREIGN PATENT DOCUMENTS

| EP | 0595148 A1 | 5/1994 |
|---|---|---|
| WO | 03049614 A1 | 6/2003 |

OTHER PUBLICATIONS

International Preliminary Report on Patentability from corresponding PCT Patent Application Serial No. PCT/US2008/068884; Jan. 5, 2010; 6 pgs.

(Continued)

*Primary Examiner* — Kathleen Holwerda
*Assistant Examiner* — Sarah W Aleman
(74) *Attorney, Agent, or Firm* — Gardner Groff Greenwald & Villanueva, PC (57) ABSTRACT

A lancet having a lancet body and a sharp lancing tip extending from the lancet body, the lancet body including at least one flexing engagement fin, which is resiliently deformable upon insertion into a receiver of a lancing device. The outer dimension of the lancet effectively self-adjusts to conform to a wide range of receiver inner dimensions, and as such, the lancet of the present invention enables universal application with a larger range of lancing devices than previously known lancets.

31 Claims, 6 Drawing Sheets

(56) References Cited

U.S. PATENT DOCUMENTS

| | | |
|---|---|---|
| 5,324,303 A | 6/1994 | Strong et al. |
| 5,569,286 A | 10/1996 | Peckham et al. |
| 7,153,318 B2 * | 12/2006 | Marshall et al. ............. 606/181 |
| 2003/0109895 A1 * | 6/2003 | Taylor et al. ................. 606/181 |
| 2005/0131441 A1 | 6/2005 | Iio et al. |
| 2006/0235454 A1 | 10/2006 | LeVaughn et al. |
| 2007/0162065 A1 * | 7/2007 | Li et al. ........................ 606/182 |

OTHER PUBLICATIONS

Extended European Search Report for EP 08772294.8; Dec. 2, 2011; 4 pgs.

* cited by examiner

VARIABLE FIT LANCET

CROSS-REFERENCE TO RELATED APPLICATION

This application claims the priority benefit of U.S. Provisional Patent Application Ser. No. 60/947,688, filed Jul. 3, 2007, the entirety of which is hereby incorporated herein by reference.

TECHNICAL FIELD

The present invention relates generally to medical devices, and more particularly to a lancet for blood sampling.

BACKGROUND OF THE INVENTION

Lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. A lancet is typically propelled by the drive mechanism from a retracted position shielded within the housing to an extended position wherein a sharp tip portion of the lancet projects from the housing to prick the subject's skin at a desired lancing site. Many lancing devices further include a depth-control mechanism for varying the depth of penetration, for example by limiting the stroke of the lancet, or by adjusting the position of an endcap or other portion of the device relative to the lancet's path of travel.

The lancet is commonly a disposable and replaceable component that is removably mounted into a receiver or lancet carrier portion of the drive mechanism of the lancing device. A used lancet typically is removed from the lancet carrier after use and disposed of. A new, sterile lancet is then replaced into the lancet carrier for subsequent use. Lancets typically comprise a sharp metal tip in the form of a needle or blade. The needle or blade is typically embedded in a substantially rigid plastic body that has a size and shape configured for releasable engagement in the receiver or lancet carrier of a specified lancing device. The sharp tip of the lancet is typically embedded in a removable plastic shroud or cap to maintain sterility and prevent inadvertent sticks prior to use. The endcap and the body of the lancet may be formed as a single, unitary plastic molding with a notched or necked section of reduced thickness for facilitating detachment and removal of the endcap. The endcap may be replaceable onto the lancet after use to re-cover the sharp lancet tip for safety and hygienic purposes.

Known lancets are commonly configured for use in connection only with specified models of lancing devices or only with lancing devices having particular receiver dimensions. Some lancing devices have receivers that flex or expand during loading to grip the lancet body, and thus may accommodate lancets of varying dimensions, but typically only within a fairly narrow tolerance range. Thus, known lancets typically do not fit universally in different lancing devices that have a large variation of lancet receiver dimensions. For example, a lancing device having a receiver suited for lancets of 6-7 mm body diameter typically cannot receive a lancet having a body diameter of 8 mm, and will not grip a lancet having a body diameter of 5 mm. As such, users must be careful to select the correct size of lancet for their intended model of lancing device. This may present a challenge for users having reduced visual acuity. And a user having purchased lancets of incorrect size may be unable to test their blood sugar until lancets of the correct size can be obtained, possibly leading to adverse health effects.

SUMMARY OF THE INVENTION

In example forms, the present invention is an improved lancet that is universally adaptable for use in connection with lancing devices having a larger variation of lancet receiver geometry than previously known lancets. As such, a single model of lancet is compatible with a larger variety of lancing devices than previously permitted. For users, this reduces the likelihood of purchasing incorrect lancets, and reduces the difficulty involved in selecting the proper lancet for their lancing device. For sellers and manufacturers, fewer lancet models need to be produced or stocked in inventory for compatibility with a desired range of lancing devices.

In one aspect, the present invention is a lancet including a lancet body and a sharp lancing tip extending from the lancet body, the lancet body having at least one flexing engagement fin, whereby the at least one flexing engagement fin is resiliently deformable upon insertion into a receiver of a lancing device.

In another aspect, the invention is a lancet including a body and a sharp lancet tip. The body of the lancet preferably includes a plurality of outwardly projecting engagement fins, each of the plurality of outwardly projecting engagement fins having a base edge and a free edge, the free edge being flexibly movable relative to the base edge between an unflexed state and a flexed state. In this manner, the free edges of the outwardly projecting engagement fins are circumscribable within a first receiver periphery in their unflexed state and are circumscribable within a second receiver periphery in their flexed state. The first receiver periphery defines a first peripheral dimension and the second receiver periphery defines a corresponding second peripheral dimension, with the first peripheral dimension being larger than the second peripheral dimension, such that the lancet can be securely engaged within lancing device receivers of varying sizes.

In still another aspect, the invention is a lancet including a body having a central core with four flexible engagement fins projecting outwardly therefrom along at least a portion of the central core's length. Each of the four flexible engagement fins preferably has a root edge attached to the central core and a free edge distal its root edge. The root edge preferably defines a first thickness and the free edge preferably defines a second thickness, and the first thickness is greater than the second thickness. In this manner, the engagement fins are stiffer toward their roots, and more flexible toward their tips.

These and other aspects and features of the invention will be understood with reference to the drawing figures and detailed description herein, and will be realized by means of the various elements and combinations particularly pointed out in the appended claims.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Although example forms of the invention may be described in terms of a combination of various elements or steps, the invention also includes the elements or steps individually and in any subcombination thereof. As used in the specification including the appended claims, the singular forms "a," "an," and "the" include the plural as well as the singular, and reference to a particular numerical value includes embodiments having at least that particular value, unless the context clearly dictates otherwise. Ranges may be expressed herein as from "about" or "approximately" one particular value and/or to "about" or "approximately" another particular value, which terms are to be interpreted as they would be understood by one of ordinary skill in the art. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, FIGS. 1-5 show a lancet 10 according to a first example form of the invention. The lancet 10 includes a lancet body 12, and a sharp lancet tip 14. The lancet body 12 comprises a generally elongate body extending along a lengthwise axis A. In the depicted embodiment, the lancet tip 14 extends along the lengthwise axis. In alternate embodiments, the lancet tip may be eccentrically mounted relative to the lengthwise axis. The lancet body 12 may be generally circumscribed within an imaginary cylindrical boundary represented by reference circle C projected along axis A.

The lancet body 12 comprises a central core 20, having one or more ribs or fins projecting therefrom for engagement within the lancet carrier or receiver 40 of a lancing device. In the depicted embodiment, four flexing fins 22a, 22b, 22c and 22d project from the central core 20 in two opposed pairs, forming a generally H-shaped cross-section. The outer edges of the four flexing fins 22a, 22b, 22c and 22d are coincident with the reference circle C, which preferably has a diameter equal to or slightly greater than the inside diameter of the lancet carrier or receiver 40 of maximum size within the range of intended application. For example, if the inside lancet carrier diameters of the intended range of application are from 6 mm to 8 mm, the outer edges of the four flexing fins 22a, 22b, 22c and 22d are coincident with a reference circle C having a diameter of at least about 8 mm.

Distal or rear ends 24 of the fins 22 preferably comprise a progressively narrowing taper in the lengthwise direction, for ease of insertion into the lancet carrier; and medial portions of the fins optionally taper in a progressively widening fashion therefrom along the length of the fins (i.e., in a direction parallel to axis A) for more secure engagement with the lancet carrier or receiver 40 upon installation, as described below. Optionally, the fins 22 are thicker in cross-section toward their root or point of attachment to the core 20 of the lancet, and thinner in cross-section toward their tip or free edge, in the form of a continuously tapering or stepped profile, thereby providing a progressively increasing degree of flexure along their depth. In the depicted embodiment, the four flexing alignment fins are arranged in two diametrically opposed pairs, an upper pair comprising fins 22a and 22b, and a lower pair comprising fins 22c and 22d, forming a generally H-shaped cross-sectional configuration. In relation to the central axis A, the points of contact against the inner face of the receiver of the fins of each pair (see FIG. 5) are spaced about 55° from one another, and the points of contact against the inner face of the receiver of the diametrically opposite fins are spaced about 125° from one another. Preferably, the spacing between receiver-contacting points of adjacent fins is between about 30° to about 150°.

Figure 1:
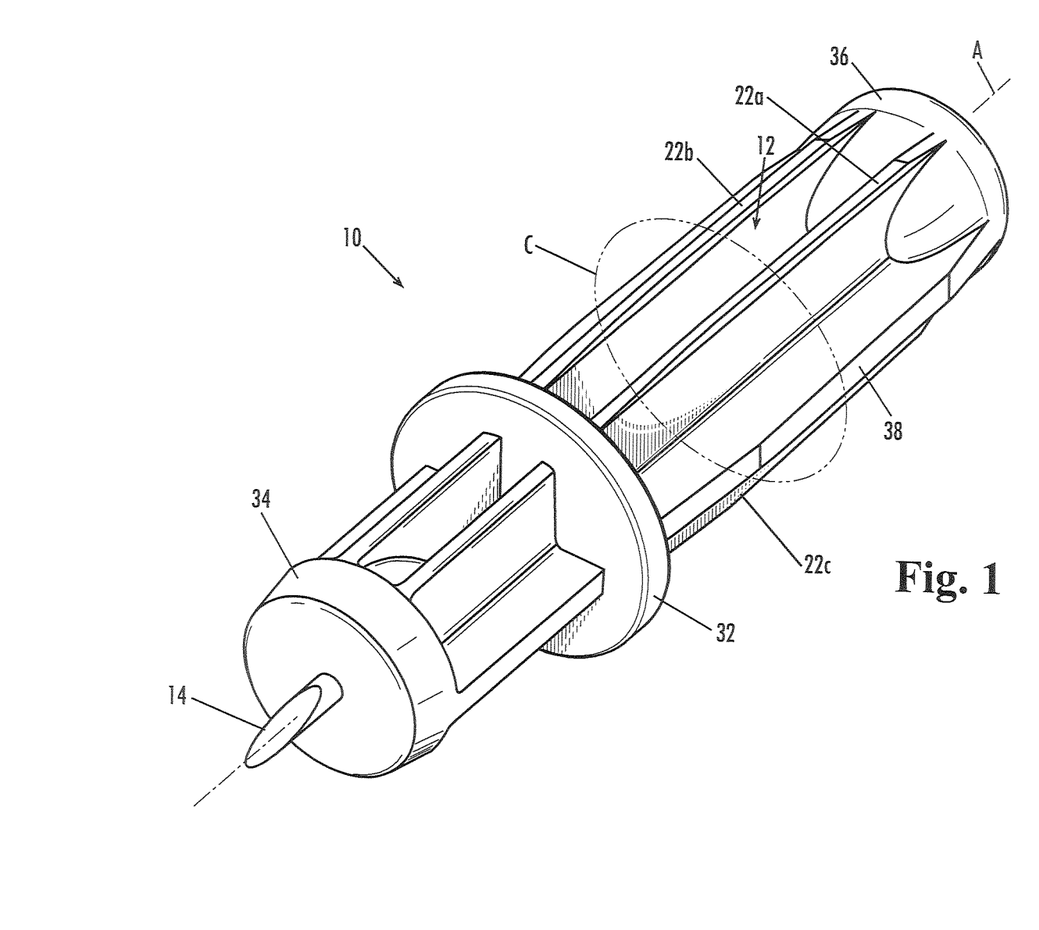
FIG. 1 is a perspective view of a lancet according to an example form of the invention.
Figure 2:
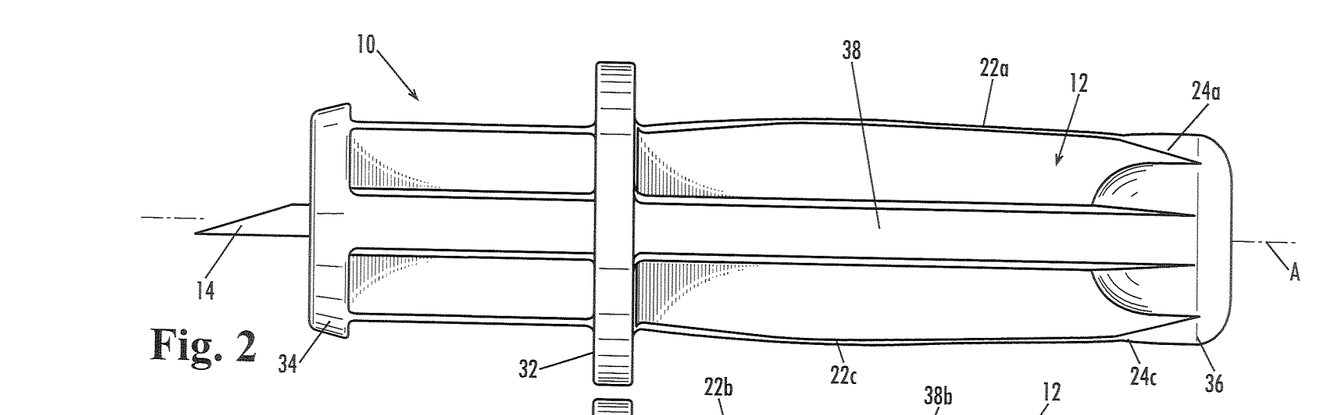
FIG. 2 is a side view of the lancet of FIG. 1.
Figure 3:
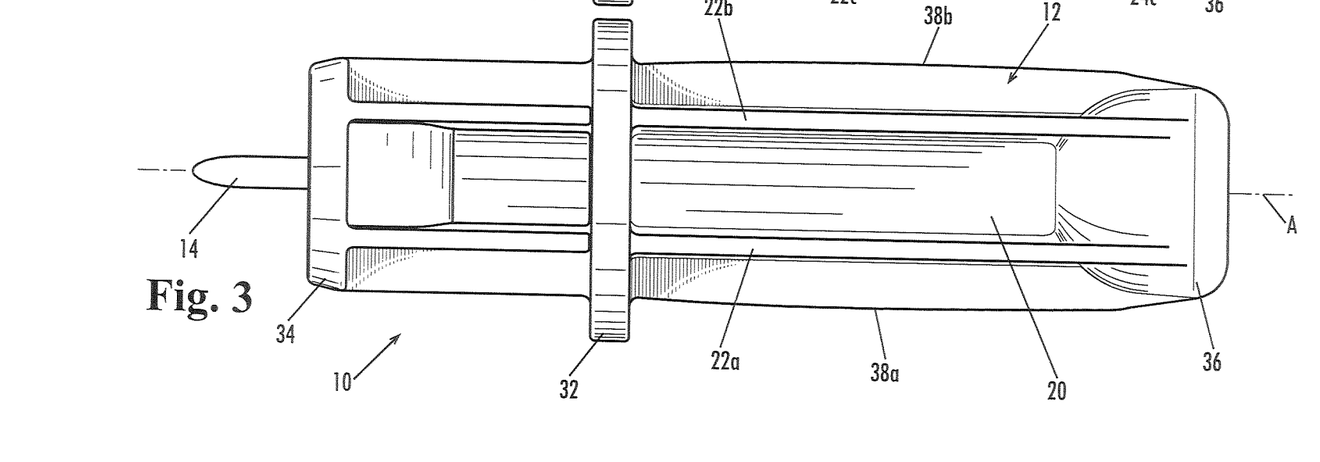
FIG. 3 is a top view of the lancet of FIG. 1.
Figure 4:
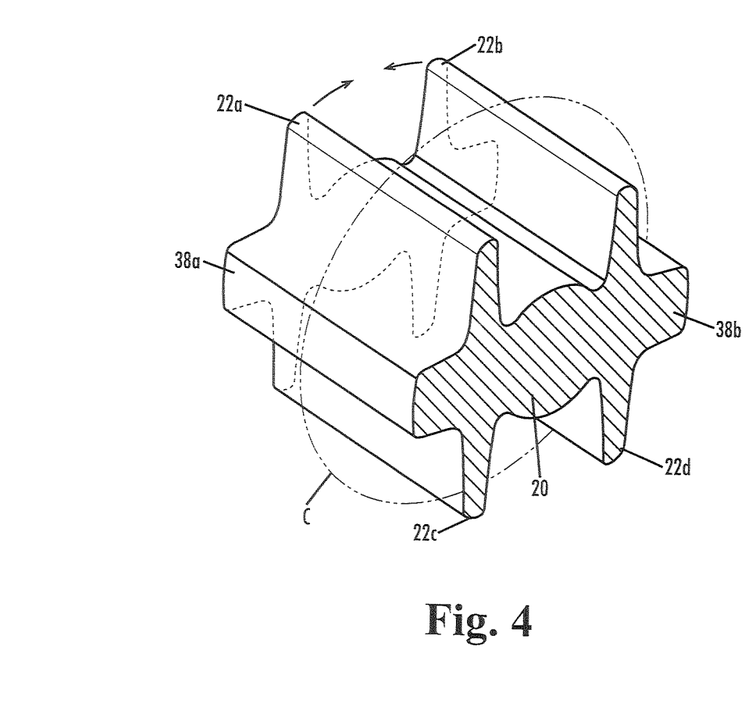
FIG. 4 is a perspective cutaway view of a body segment of the lancet of FIG. 1.

The lancet body 12 optionally further comprises a radially outwardly extending stop ring or flange 32 to assist in gripping the lancet during installation into the lancet carrier, and to provide consistent alignment and seating of the lancet in the carrier. The stop ring 32 preferably has an outer diameter or crosswise dimension that is greater than the inside diameter of the lancet carrier or receiver of maximum size within the range of intended application. Thickened body portions 34, 36 are optionally provided at the forward and back ends of the lancet body, respectively. One or more stiffening ribs 38 can optionally be provided along the lancet body 12 to stiffen the lancet and to assist in gripping the lancet during installation into a lancing device. In the depicted embodiment, a diametrically opposed pair of stiffening ribs 38a, 38b are provided. The stiffening ribs preferably extend outwardly from the body core 28 to a lesser extent than the flexing engagement fins 22, and define an outer dimension or diameter that is equal to or less than the inside diameter of the lancet carrier or receiver 40 of minimum size within the range of intended application. For example, if the inside lancet carrier diameters of the intended range of application are from 6 mm to 8 mm, the outer faces of the stiffening ribs 38 define an outer dimension of no more than about 6 mm. The lancet 10 optionally also comprises a removable endcap (unshown) for shielding the sharp lancet tip 14 prior to and/or after use.

Figure 5:
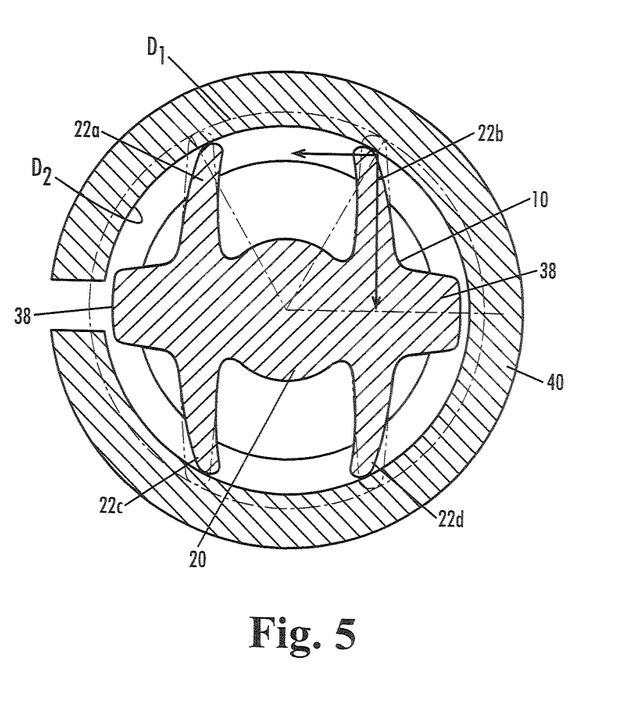
FIG. 5 is a cross-sectional view of the lancet of FIG. 1, engaged in a receiver of a lancing device in typical fashion.
Figure 6:
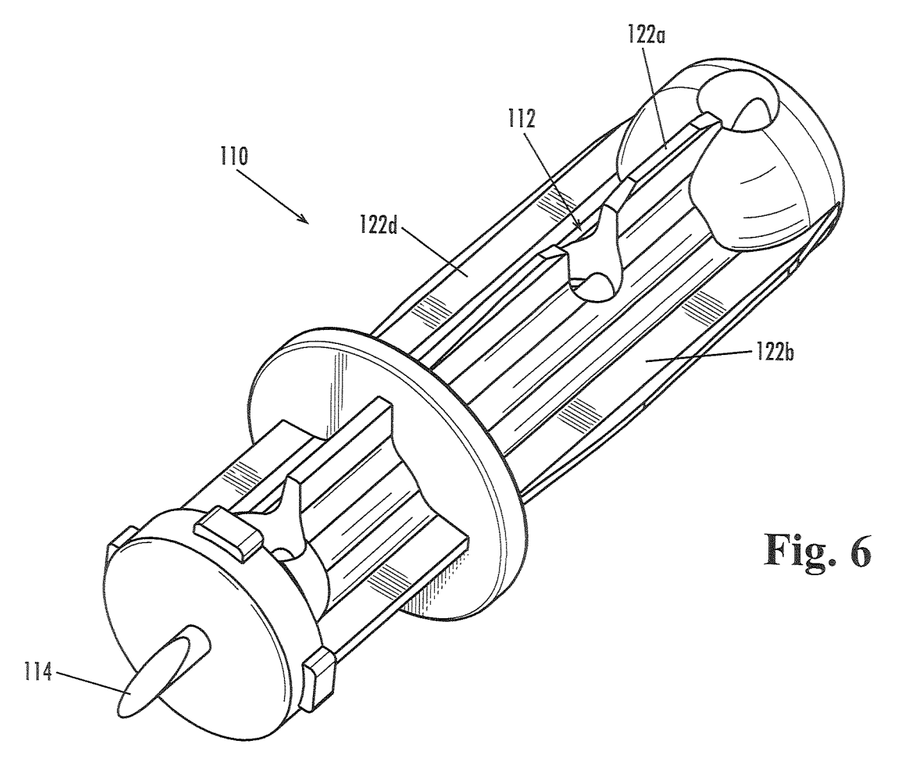
FIG. 6 is a perspective view of a lancet according to another example form of the invention.
Figure 7:
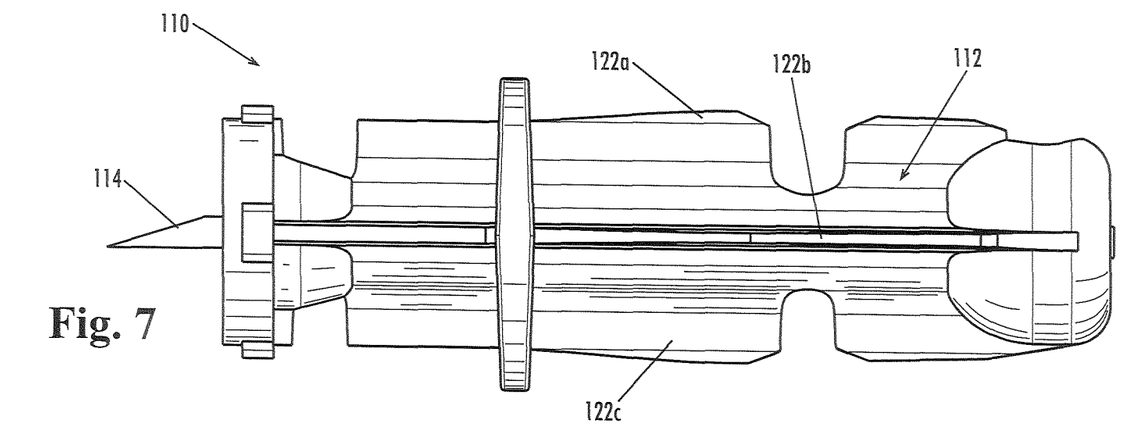
FIG. 7 is a side view of the lancet of FIG. 6.
Figure 8:
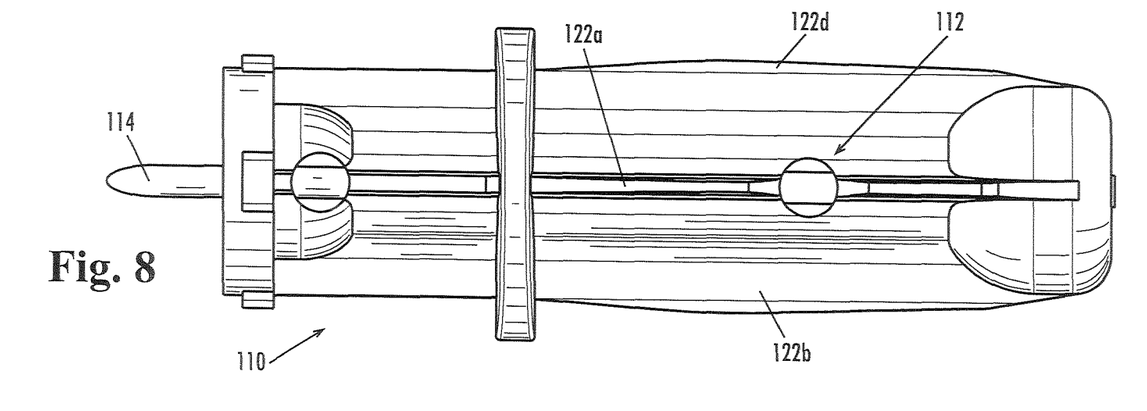
FIG. 8 is a top view of the lancet of FIG. 6.
Figure 9:
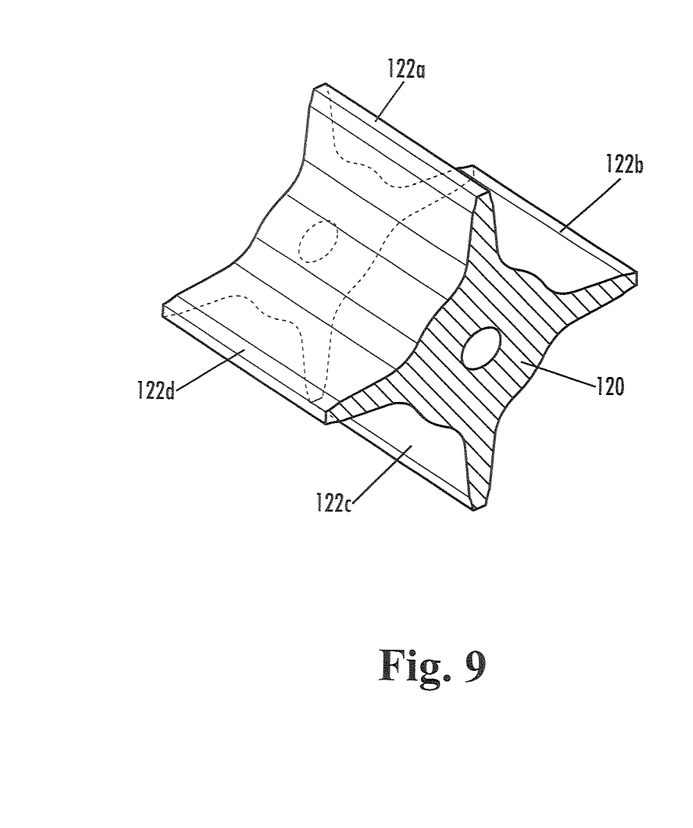
FIG. 9 is a perspective cutaway view of a body segment of the lancet of FIG. 6.
Figure 10:
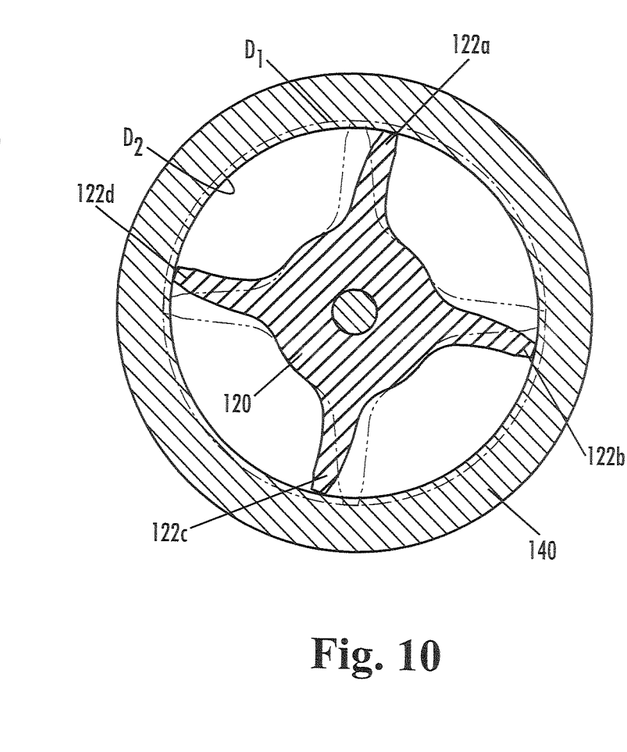
FIG. 10 is a cross-sectional view of the lancet of FIG. 6, engaged in a receiver of a lancing device in typical fashion.

In use, the lancet 10 is installed into a lancing device by insertion of the back end 36 of the lancet into the opening of the lancet carrier or receiver 40. As shown in FIG. 5, the outer edges of the flexing engagement fins 22 contact and engage with the inner face of the receiver 40, to securely retain the lancet in the lancing device. At least the flexing engagement fins 22 of the lancet body are formed of a resiliently deformable material, such as a soft plastic or rubber, which allows the flexing engagement fins to deform inwardly as needed upon insertion into the receiver 40. Thus, in their undeformed or unflexed state (shown in broken lines in FIG. 5) the fins are circumscribable within a first outer periphery, and in their deformed or flexed state (shown in solid lines in FIG. 5) the fins are circumscribable within a second outer periphery, the first outer periphery having a first circumference or peripheral dimension $D_1$ that is greater than a corresponding second circumference or peripheral dimension $D_2$ of the second outer periphery. In preferred form, the stiffness of the flexing engagement fins 22 is sufficiently low to impact the forces necessary for insertion and removal of the lancet into the lancing device to only a minimal or moderate extent. In this manner, the outer dimension of the lancet effectively self-adjusts to conform to a wide range of receiver inner dimensions, and maintain the lancet tip centrally aligned within the receiver 40. As such, the lancet 10 of the present invention enables universal application with a larger range of lancing devices than previously known lancets.

FIGS. 6-10 show a lancet 110 according to another embodiment of the present invention. The lancet 110 is generally similar in construction and manner of use to lancet 10 described above, the primary distinction being in the arrangement of the flexing engagement fins. The lancet 110 generally includes a lancet body 112, and a sharp lancet tip 114. The lancet body 112 further comprises a central core 120, with four flexing fins 122a, 122b, 122c and 122d projecting generally radially therefrom, and extending along at least a portion of the length of the lancet body. As seen best with reference to FIGS. 9 and 10, the fins 122 of this embodiment are arranged in a generally crosswise or X-shaped configuration, with each fin oriented at about 90° from adjacent fins, when viewed end-on or in cross-section. In this manner, the contact points between the receiver 140 of the lancing device and the fins 122 are generally evenly circumferentially spaced, at about 90° intervals.

In the depicted embodiments, the flexing engagement fins take the form of elongate ribs extending axially along the lancet body, generally parallel to the lengthwise axis A. In alternate embodiments, the one or more flexing engagement fins may take various other forms, including without limitation, one or more radially outwardly extending flexible rings or flanges spaced along the length of the lancet body, one or more helical flexible fins, or one or more arrays of flexing fingers extending outwardly from the lancet body. Also, while four flexing engagement fins are depicted in the example embodiment shown in the figures, the present invention includes embodiments having two, three, or greater than four engagement fins; as well as four-fin embodiments having various alternate configurations in terms of spacing between the fins and/or angular orientation of the fins. For example, in an example three-fin embodiment of the invention, each of the three flexing engagement fins is spaced about 120° from the adjacent fins, and is directed radially outwardly from the central axis of the lancet core. In example forms of the invention, the flexing engagement fins are generally equally or symmetrically spaced, thereby providing substantially even deformation of the fins relative to the central axis of the lancet, and maintaining consistent alignment of the lancet tip in relation to the receiver of the lancing device.

While the invention has been described with reference to preferred and example embodiments, it will be understood by those skilled in the art that a variety of modifications, additions and deletions are within the scope of the invention, as defined by the following claims.

What is claimed is:

1. A lancet comprising a lancet body having a proximal end and a distal end, and a sharp lancing tip extending from the proximal end of the lancet body, the lancet body comprising at least one flexing engagement fin comprising a forward end and a rear end, the at least one flexing engagement fin extending from adjacent the distal end of the lancet body at least to about a midpoint between the proximal and distal ends of the lancet body and being in substantially continuous attachment with the lancet body between the forward and rear ends thereof, wherein the lancet body comprises a longitudinal axis, whereby the at least one flexing engagement fin deforms circumferentially about the lancet body longitudinal axis upon insertion into a receiver of a lancing device.

2. The lancet of claim 1, further comprising at least one stiffening rib extending along the lancet body.

3. The lancet of claim 1, comprising at least three flexing engagement fins.

4. The lancet of claim 1, comprising four flexing engagement fins.

5. The lancet of claim 4, wherein the four flexing engagement fins are arranged to define a generally H-shaped fin configuration.

6. The lancet of claim 4, wherein the four flexing engagement fins are arranged to define a generally X-shaped fin configuration.

7. The lancet of claim 4, wherein a medial portion of each flexing engagement fin tapers in a progressively widening fashion from the rear end.

8. The lancet of claim 1, wherein each flexing engagement fin is thicker at a base edge thereof and thinner at a free edge thereof, thereby providing a progressively increasing degree of flexure.

9. The lancet of claim 1, further comprising a radially outwardly extending stop member to provide consistent seating of the lancet in the receiver.

10. The lancet of claim 1, wherein the lancet body comprises at least one pair of flexing engagement fins, each flexing engagement fin in the pair is configured to flex inwardly toward the other.

11. A lancet comprising a body having a proximal end and a distal end, and a sharp lancet tip extending from the proximal end of the body, the body having a longitudinal axis, the body of the lancet comprising a plurality of outwardly projecting engagement fins, each of the plurality of outwardly projecting engagement fins having a forward end and a rear end, wherein each engagement fin extends from adjacent the distal end of the lancet body at least to about a midpoint between the proximal and distal ends of the lancet body, each of the plurality of outwardly projecting engagement fins having a base edge and a free edge, the base edge being in substantially continuous attachment with the lancet body between the forward and rear ends of each engagement fin, and the free edge being flexibly movable relative to the base edge between an unflexed state and a flexed state, wherein the free edge is configured to flex circumferentially about the body longitudinal axis, whereby the free edges of the outwardly projecting engagement fins are circumscribable within a first receiver periphery in their unflexed state and are circumscribable within a second receiver periphery in their flexed state, the first receiver periphery defining a first peripheral dimension and the second receiver periphery defining a corresponding second peripheral dimension, the first peripheral dimension being larger than the second peripheral dimension.

12. The lancet of claim 11, wherein the plurality of outwardly projecting engagement fins comprises at least three outwardly projecting engagement fins.

13. The lancet of claim 11, wherein the plurality of outwardly projecting engagement fins comprises four outwardly projecting engagement fins.

14. The lancet of claim 11, wherein the four outwardly projecting engagement fins are arranged in two diametrically opposed pairs forming a generally H-shaped configuration.

15. The lancet of claim 11, wherein the four outwardly projecting engagement fins are radially oriented and form a generally X-shaped configuration.

16. The lancet of claim 11, wherein the plurality of outwardly projecting engagement fins are angularly spaced at between about 30° to about 150° between one another.

17. The lancet of claim 11, wherein the plurality of outwardly projecting engagement fins are angularly spaced at about 90° between one another.

18. The lancet of claim 11, wherein the base edge of each of the plurality of outwardly projecting engagement fins is thicker than the free edge, thereby providing an increasing degree of flexure toward the free edge.

19. The lancet of claim 11, wherein a medial portion of each of the plurality of outwardly projecting engagement fins tapers in a progressively widening fashion from the rear end.

20. The lancet of claim 11, further comprising a radially outwardly extending stop member.

21. The lancet of claim 11, further comprising at least one stiffening rib extending along the lancet body.

22. The lancet of claim 11, wherein each of the plurality of engagement fins is configured to flex toward another of the plurality of engagement fins.

23. A lancet comprising a body having a proximal end, a distal end, and a longitudinal central core with four flexible engagement fins projecting outwardly therefrom along at least a portion of the central core's length, each of the engagement fins having a length extending from adjacent the distal end of the lancet body at least to about a midpoint between the proximal and distal ends of the lancet body, each of the four flexible engagement fins having a root edge continuously attached to the central core along substantially the entire length of the fin and a free edge directed outwardly from the root edge, the root edge defining a first thickness and the free edge defining a second thickness, the first thickness being greater than the second thickness, wherein each of the four flexible engagement fins is configured to deflect circumferentially about the longitudinal central core.

24. The lancet of claim 23, wherein the four flexible engagement fins are arranged in two diametrically opposed pairs forming a generally H-shaped configuration.

25. The lancet of claim 23, wherein the four flexible engagement fins are radially oriented and form a generally X-shaped configuration.

26. The lancet of claim 23, wherein the four flexible engagement fins define a fin depth between the root edge and the free edge, and wherein the fin depth tapers inwardly toward a proximal end of the lancet.

27. The lancet of claim 23, further comprising at least one stiffening rib extending along the lancet body.

28. The lancet of claim 23, further comprising a circumferential stop ring extending radially outwardly from the central core.

29. The lancet of claim 23, wherein the four flexible engagement fins are angularly spaced at between about 30° to about 150° from one another.

30. The lancet of claim 23, wherein the four flexible engagement fins are angularly spaced at about 90° between one another.

31. The lancet of claim 23, wherein each of the flexible engagement fins is configured to flex toward another of the four flexible engagement fins.

* * * * *